US011983833B2

(12) United States Patent
Moodley (10) Patent No.: US 11,983,833 B2
(45) Date of Patent: May 14, 2024

(54) COMPUTER-IMPLEMENTED METHOD OF GENERATING AN AVATAR

(71) Applicant: Health Connect Global Limited, Manchester (GB)

(72) Inventor: Devan Moodley, Manchester (GB)

(73) Assignee: HEALTH CONNECT GLOBAL LIMITED, Manchester (GB)

( * ) Notice: Subject to any disclaimer, the term of this patent is extended or adjusted under 35 U.S.C. 154(b) by 90 days.

(21) Appl. No.: 17/657,161

(22) Filed: Mar. 30, 2022

(65) Prior Publication Data

US 2023/0316686 A1 Oct. 5, 2023

(51) Int. Cl.
*G06T 19/20* (2011.01)
*G16H 10/60* (2018.01)
*G16H 50/20* (2018.01)

(52) U.S. Cl.
CPC ............ *G06T 19/20* (2013.01); *G16H 10/60* (2018.01); *G16H 50/20* (2018.01); *G06T 2200/24* (2013.01); *G06T 2210/41* (2013.01); *G06T 2219/004* (2013.01);
(Continued)

(58) Field of Classification Search
CPC . G06T 19/20; G06T 2200/24; G06T 2210/41; G06T 2219/004; G06T 2219/2012; G06T 2219/2016; G06T 2219/2021; G06T 11/60; G06F 3/011; G06F 3/012; G06F 3/017; G06F 3/0428; G16H 10/60; G16H 50/20; G16H 15/00; G16H 30/20; G16H 30/40; G06N 3/045; G06N 3/08; G06N 20/00
See application file for complete search history.

(56) References Cited

U.S. PATENT DOCUMENTS 9,805,381 B2 * 10/2017 Frank ................. G06F 16/337
10,037,820 B2 * 7/2018 Wong ................. G16H 50/50
11,269,891 B2 * 3/2022 Frank ................. G06F 16/904
(Continued)

FOREIGN PATENT DOCUMENTS

CN 110689521 A 1/2020
WO 2017160920 A1 9/2017

OTHER PUBLICATIONS

PCT International Search Report and Written Opinion for International Application No. PCT/GB2023/050668, dated May 30, 2023, 17 pages.
(Continued)

*Primary Examiner* — Vijay Shankar
(74) *Attorney, Agent, or Firm* — Hoffman Warnick LLC (57) ABSTRACT

There is provided a computer-implemented method of annotating an avatar representative of a human body with medical information associated with a patient, the method performed by a computer including a hardware processor, the method comprising: providing, by the hardware processor, the avatar; retrieving, by the hardware processor, electronic data from a blockchain, the electronic data describing the medical information; applying the electronic data, by the hardware processor, to one or more machine learning algorithms trained to associate the medical information with a body part from amongst a plurality of body parts of the human body; and annotating, by the hardware processor, the avatar with the medical information at a location of the associated body part.

18 Claims, 4 Drawing Sheets

(52) U.S. Cl.
CPC .............. *G06T 2219/2012* (2013.01); *G06T 2219/2016* (2013.01); *G06T 2219/2021* (2013.01)

(56) References Cited

U.S. PATENT DOCUMENTS

| | | |
|---|---|---|
| 11,494,390 B2 * | 11/2022 | Frank .................. G06F 16/907 |
| 2013/0325493 A1 | 12/2013 | Wong et al. |
| 2017/0173262 A1 * | 6/2017 | Veltz ...................... G16H 20/17 |
| 2020/0293174 A1 | 9/2020 | Diaz et al. |
| 2020/0294677 A1 | 9/2020 | Godinho et al. |
| 2023/0024672 A1 * | 1/2023 | Bonutti ................ G06F 21/602 |

OTHER PUBLICATIONS

Shi et al., "Applications of blockchain in ensuring the security and privacy of electronic health record systems: A survey," Computer & Security 97 (2020), Elsevier, 20 pages.

Ramachandran et al., "A Review on Blockchain-Based Strategies for Management of Electronic Health Records (EHRs)," 2020 International Conference on Smart Electronics and Communication, Oct. 7, 2020, 341-346.

Agbo et al., "Blockchain Technology in Healthcare: A Systematic Review," Healthcare, vol. 7, No. 2, 4 Apr. 4, 2019, p. 56.

* cited by examiner

COMPUTER-IMPLEMENTED METHOD OF GENERATING AN AVATAR

TECHNICAL FIELD

The subject-matter of the present disclosure relates to a computer-implemented method of annotating an avatar representative of a human body with medical information. The subject-matter of the present disclosure also relates to a computer-implemented method of generating a patient-specific avatar.

BACKGROUND

It is important to maintain confidentiality of patients' medical records. Use of a blockchain is one method by which data, such as medical information, can be securely managed.

However, managing medical information using a blockchain causes problems in easily accessing and viewing the medical information. For example, it may be difficult for a medical practitioner to efficiently access and view a patient's medical information in an understandable (e.g., human readable) format if this this information is stored on a blockchain.

The aim of the present disclosure is to address such problems and improve on the prior art.

SUMMARY

It is one aim of the present disclosure, amongst others, to provide a computer-implemented method of annotating an avatar representative of a human body with medical information associated with a patient and a computer-implemented method of generating a patient-specific avatar which at least partially obviate or mitigate at least some of the disadvantages of the prior art, whether identified herein or elsewhere, or to provide an alternative approach. For instance, it is an aim of embodiments of the disclosure to provide a computer-implemented method of annotating an avatar representative of a human body with medical information associated with a patient that enables secure management of medical information while simultaneously enabling efficient access of this medical information.

According to a first aspect, there is provided a computer-implemented method of annotating an avatar representative of a human body with medical information associated with a patient performed by a computer including a hardware processor. The method comprises providing, by the hardware processor, the avatar; retrieving, by the hardware processor, electronic data from a blockchain, the electronic data describing the medical information; applying the electronic data, by the hardware processor, to one or more machine learning algorithms trained to associate the medical information with a body part from amongst a plurality of body parts of the human body; and annotating, by the hardware processor, the avatar with the medical information at a location of the associated body part. Advantageously, this method facilitates automated, secure and efficient provision of medical information to, for example, a medical practitioner.

In one embodiment, the medical information comprises at least one of: text and an image. Advantageously, the method is usable with text and images, which covers vast amounts of medical information.

In one embodiment, when the medical information comprises an image, the image comprises at least one of: a radiogram, a tomogram, a thermogram, a magnetic resonance imaging scan image, a positron emission tomography scan image, an ultrasound image, a photoacoustic image, a retinal image and an elastogram.

In one embodiment, the one or more machine learning algorithms comprises a neural network.

In one embodiment, the computer-implemented method further comprises, when the medical information comprises text, pre-processing, by the hardware processor, the retrieved electronic data to tokenise the text. Advantageously, the medical information is easier to process and the processing time can thus be reduced whilst the accuracy of classification is improved.

In one embodiment, the computer-implemented method further comprises applying, by the hardware processor, the retrieved electronic data to an unsupervised clustering algorithm to cluster the retrieved electronic data into groups, where each group is associated with a body part. Advantageously, efficiency of the method is engendered, because the annotating can be performed for multiple pieces of medical information relating to a particular body part using a reduced number of steps.

In one embodiment, annotating the avatar comprises retrieving, by the hardware processor, an anatomical region of the avatar corresponding to the location of the body part; and storing, by the hardware processor, the medical information at the anatomical region on the avatar. A look-up table and node arrangement, for instance, is a simple mechanism enabling the annotations and is easily modifiable in an event that more nodes are required at a location of high density of medical information, e.g., the chest area. Storing the medical data locally can aid building a long-term view of the patient's medical status to aid in disease prognosis assessment.

In one embodiment, the computer-implemented method may further comprise displaying, by the hardware processor, the annotation when a user input device is located over the anatomical region; and concealing, by the hardware processor, the annotation when the user input device is not located over the anatomical region.

Advantageously, there is no need to input search terms such that there is no dependency on keywords to obtain required information. In this way, the annotated avatar can be easily interrogated in an intuitive manner reducing the training burden of medical professionals.

In one embodiment, the avatar comprises a plurality of nodes defined by spatial coordinates, wherein the associated body part includes one or more of the plurality of nodes, and wherein the location of the associated body part is associated with one of the plurality of nodes.

In one embodiment, the avatar is rotatable about at least one of: the sagittal plane, the coronal plane and the transverse plane. Advantageously, the method benefits of the method are realised for any part of the human anatomy in three dimensions. Thus, certain parts of the avatar are easier to interrogate.

According to a second aspect, there is provided a computer-implemented method of generating a patient-specific avatar performed by a computer including a hardware processor. The method comprises providing, by the hardware processor, a generic avatar representative of a human body; retrieving, by the hardware processor, electronic data from a blockchain, the electronic data describing medical information associated with a patient; applying, by the hardware processor, the electronic data, by the hardware processor, to one or more machine learning algorithms trained to determine a change to a body part of the generic avatar based on the medical information; and generating the patient-specific avatar by modifying the generic avatar based on the determined change. Advantageously, this method facilitates automated, secure and personalised provision of medical information to, for example, a medical practitioner. In this way, the patient specific avatar can provide a more intuitive representation to the medical practitioner of the patient's condition (e.g., obesity).

In one embodiment, wherein the medical information comprises at least one of: text and an image.

In one embodiment, when the medical information comprises an image, the image comprises at least one of: a radiogram, a tomogram, a thermogram, a magnetic resonance imaging scan image, a positron emission tomography scan image, an ultrasound image, a photoacoustic image, a retinal image and an elastogram.

In one embodiment, the one or more machine learning algorithms comprises a neural network.

In one embodiment, the computer-implemented method further comprises applying the retrieved electronic data to an unsupervised clustering algorithm to cluster the retrieved electronic data into groups, where each group is associated with a body part.

In one embodiment, modifying the patient-specific avatar comprises retrieving, by the hardware processor, a shape representing the change to the body part; and modifying, by the hardware processor, the generic avatar to include the shape representing the change to the body part. Advantageously, using a change of shape is a computationally efficient way to change the avatar.

In one embodiment, the modifying the generic avatar comprises at least one of: translating, scaling, rotating and colouring at least a part of the generic avatar. Advantageously, a plethora of medical conditions can be represented by the avatar.

In one embodiment, the generic avatar comprises a plurality of nodes defined by spatial coordinates, wherein the body part includes one or more of the plurality of nodes.

In one embodiment, the patient-specific avatar is rotatable about at least one of: the sagittal plane, the coronal plane and the transverse plane.

According to a third aspect, there is provided a non-transitory computer-readable medium including instructions stored thereon that, when executed by a hardware processor, cause the processor to perform the method of the first aspect, the second aspect, or any of the foregoing embodiments.

BRIEF DESCRIPTION OF THE DRAWINGS

For a better understanding of the disclosure, and to show how embodiments of the same may be brought into effect, reference will be made, by way of example only, to the accompanying diagrammatic Figures, in which.

DETAILED DESCRIPTION

Figure 1:
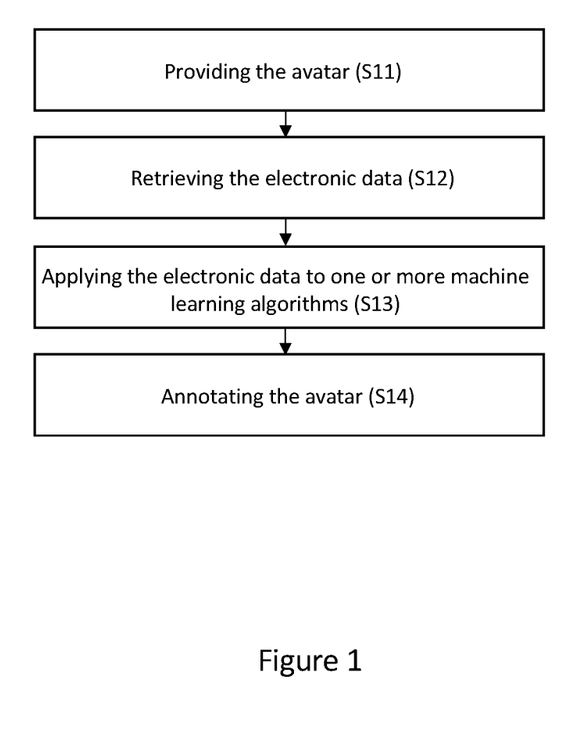
FIG. 1 schematically depicts a computer-implemented method of assigning medical information to an avatar representative of a human body performed by a computer including a hardware processor according to an exemplary embodiment.

FIG. 1 schematically depicts a computer-implemented method of annotating an avatar representative of a human body with medical information associated with a patient performed by a computer according to an exemplary embodiment. The computer may include a storage and a hardware processor. The storage may include a memory.

The computer-implemented method of FIG. 1 comprises providing, at step S11, by the hardware processor, the avatar. The avatar is a graphical representation of a human body. The avatar is a digital avatar. Providing S11 the avatar may comprise, by the hardware processor, generating the avatar. For instance, the hardware processor may generate the avatar by retrieving the avatar from a storage.

The computer-implemented method of FIG. 1 comprises retrieving, at step S12, by the hardware processor, electronic data from a blockchain, the electronic data describing the medical information. Retrieving S12 the electronic data may comprise using a blockchain explorer to crawl the blockchain to extract the electronic data. Any suitable blockchain explorer may be used. Use of a blockchain means that the medical information (e.g., patient records) are secure.

The blockchain crawler may operate periodically. In other embodiments, the blockchain crawler may operate in response to a request to provide an avatar for a specific patient. This process may occur in real-time.

The computer-implemented method of FIG. 1 may further comprise pre-processing the retrieved electronic data to tokenise text included in the medical information. In this way, the security of the medical information in maintained.

The computer-implemented method of FIG. 1 may further comprise unencrypting, by the hardware processor, the retrieved electronic data and storing the unencrypted electronic data in a database. Unencrypting the retrieved electronic data is usually performed prior to any tokenisation of text. Unencrypting the retrieved electronic data typically involves using feature extraction algorithms to remove any unwanted data, such as commas and illegible words, from the text of the medical information and to extract lexical features. In this way, the unstructured retrieved medical information described by the electronic data is given an automated structure.

Medical information may be text and/or an image. In the case of the medical information comprising one or more images, the images may be one or more of, for instance, a radiogram, a tomogram (e.g., a computer tomography scan image), a thermogram, a magnetic resonance imaging (MRI) scan image, a positron emission tomography (PET) scan image, an ultrasound image, a photoacoustic image, a retinal image and an elastogram. The medical information may comprise any type of scan, photo or image. In the case of the medical information comprising text, the text may be one or more of, for instance, contemporaneous notes and data from wearable devices worn by a patient.

The computer-implemented method of FIG. 1 comprises applying, at step S13, the electronic data, by the hardware processor, to one or more machine learning algorithms trained to associate the medical information with a body part from amongst a plurality of body parts of the human body. In other words, the one or more machine learning algorithms are trained by supervised learning to match the medical information that is described by the electronic data to a body part of the human body (e.g., leg, arm, foot, hand, head, torso, etc.). Training data for the one or more machine learning algorithms may include anatomy, physiology and diagnostics textbooks, and journal papers. For example, text describing symptoms such as "irregular pulse", or "rapid pulse", may be associated with the heart in one training example within a training data set. Similarly, text describing a diagnosis of heart arrythmia may be associated with the heart in another training example. Furthermore, in the case of images, an X-ray of the chest may be associated with the chest in another training example.

The one or more machine learning algorithms may comprise a neural network. The neural network may be a deep neural network. The deep neural network may include one or more embedding layers, a plurality of fully connected layers and an output layer. Pooling and padding layers and other commonly used layers may also be used. The output layer may include a softmax layer, for example. The softmax layer provides a plurality of output nodes, each associated with a probability and a body part being true. In the case of the medical information including an image, instead of embedding layers, the neural network may include one or more convolutional layers.

The computer-implemented method of FIG. 1 comprises annotating, at step S14, by the hardware processor, the avatar with the medical information at a location of the associated body part. In other words, a location of the avatar corresponding to the body part to which the medical information pertains is assigned the medical information. For example, if the medical information relates to a patient suffering from the condition of athlete's foot (tinea pedis). The one or more machine learning algorithms associate the medical information with the foot and the avatar is annotated at a location corresponding to the feet. Advantageously, medical information is automatically assigned to a representative of a human body.

The avatar may comprise a plurality of nodes defined by spatial coordinates (e.g., Cartesian coordinates). The coordinates may be defined with reference to an origin. The origin may be located at a point on the human body. For example, the origin may be at a centroid of the avatar. The associated body part may include one or more of the plurality of nodes and the location of the associated body part may be associated with one of the plurality of nodes. In other words, the avatar may be annotated at a location determined by one or more nodes with which the location is associated.

Annotating, at step S14, the avatar may comprise retrieving, an anatomical region of the avatar corresponding to the location of the body part. In addition, the annotating may comprise storing, by the hardware processor, the medical information at the anatomical region on the avatar. To facilitate this processor, the hardware processor may refer to a look-up table. The look-up table may provide an association between body parts of the avatar and the plurality of nodes.

The computer-implemented method shown in FIG. 1 may further comprise applying the electronic data to an unsupervised clustering algorithm. For example, the unsupervised clustering algorithm may cluster the medical information by body part. A suitable clustering method is k-means clustering. By clustering these features computational efficiency is engendered, because the annotating S14 step can be performed for multiple pieces of medical information relating to a particular body part in fewer steps, rather than performing annotating for multiple pieces of medical information relating to the same body part separately. In the case of the computer-implemented method of FIG. 1 comprising applying the electronic data to an unsupervised clustering algorithm, the method may comprise generating embeddings before clustering occurs. To this end, the embeddings may be generated using an embedding model.

The computer-implemented method of FIG. 1 may further comprise displaying, by the hardware processor, the annotation when a user input (e.g., a cursor) is located over the location of the associated body part. There is no need to input search terms such that there is no dependency on keywords to obtain required information. In other words, hovering over the associated body part with the user input device may cause display of medical information related to that anatomy. Similarly, the computer-implemented method of FIG. 1 may further comprise concealing, by the hardware processor, the annotation when the user input device is not located over the location of the associated body part.

The hardware processor may be configured to allow a user to change a view of the avatar on a display. For instance, the avatar may be rotatable about one or more of the sagittal plane (lateral), the coronal (frontal) plane and the transverse (axial) plane. For instance, the hardware processor may be configured to allow zooming in or out in response to user input. Zooming in may cause annotating, by the hardware processor, of small anatomical features. For instance, zooming in on a limb may cause annotating, by the hardware processor, of the limb's digits. In this way, it is easier for a user to interrogate the avatar because nodes in a congested area may be concealed behind other nodes in certain orientations.

Figure 2:
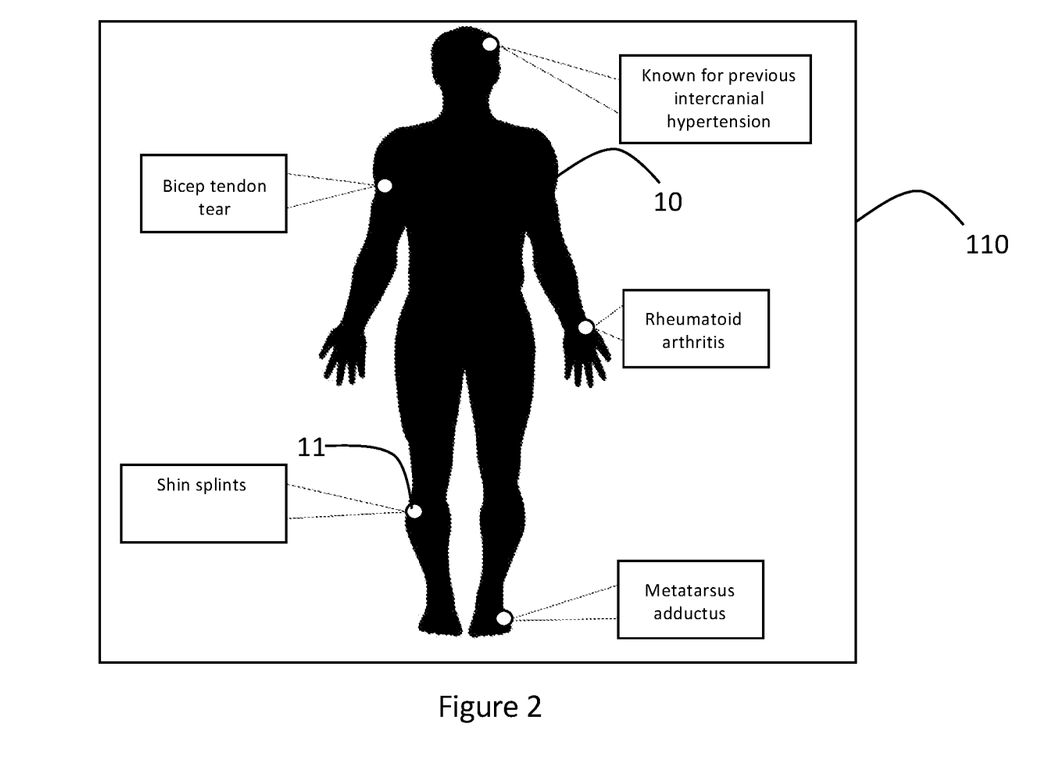
FIG. 2 schematically depicts an avatar annotated with medical information by the method shown in FIG. 1 according to an exemplary embodiment.

FIG. 2 schematically depicts an avatar annotated with medical information by the method shown in FIG. 1 according to an exemplary embodiment. The avatar 10 in FIG. 2 includes the plurality of nodes 11 at body parts with which the respective medical information is associated. The avatar shown in FIG. 2 is annotated with medical information. For example, the head of the patient is annotated with "Known for previous intercranial hypertension".

The annotated, patient specific avatar may be provided on a user interface 110. The user interface may be a mobile device (e.g., a smart phone or a tablet) or may be a display of a computer or laptop.

A non-transitory computer-readable medium including instructions stored thereon that, when executed by a hardware processor, cause the hardware processor to perform the method shown in FIG. 1 is provided.

Figure 3:
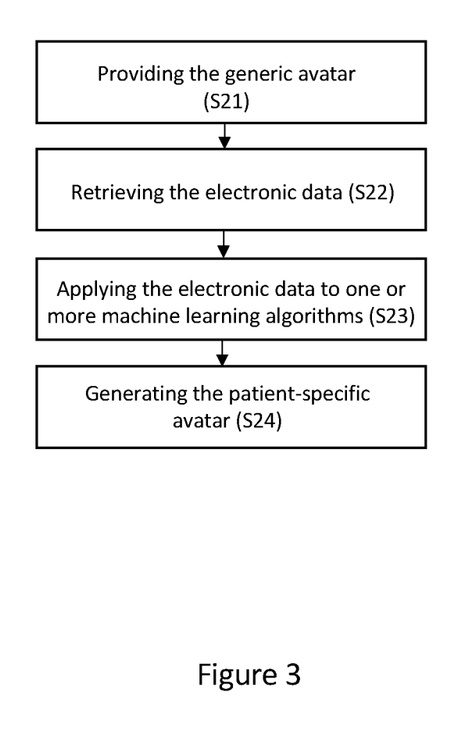
FIG. 3 schematically depicts a computer-implemented method of generating a patient-specific avatar performed by a computer including a hardware processor according to an exemplary embodiment.

FIG. 3 schematically depicts a computer-implemented method of generating a patient-specific avatar performed by a computer including a hardware processor according to an exemplary embodiment.

The computer-implemented method of FIG. 3 comprises providing, at step S21, by the hardware processor, a generic avatar representative of a human body. A generic avatar is an avatar that is not representative of a specific patient. In other words, the same generic avatar is used as a baseline avatar for every patient until it is modified based on the content of the medical data. The nature of the generic avatar and its provision is as described in relation to FIG. 1 (S11) for the avatar. FIG. 2 may be considered to show a generic avatar 10.

The computer-implemented method of FIG. 3 comprises retrieving S22, by the hardware processor, electronic data from a blockchain, the electronic data describing medical information associated with a patient. This step and the medical information are as described in relation to FIG. 1 (S12). Similarly, the computer-implemented method of FIG. 3 may comprise pre-processing, unencrypting and clustering the electronic data as described in respect of FIG. 1. The machine learning algorithm is also as described in respect of FIG. 1.

The computer-implemented method of FIG. 3 comprises applying, at step S23, the electronic data, by the hardware processor, to one or more machine learning algorithms trained to determine a change to a body part of the generic avatar based on the medical information. That is, the one or more machine learning algorithms use the medical information to determine how a body part of the generic avatar should be changed in order that the generic avatar is personalised to the patient to whom the medical information relates.

Characteristics represented by the generic avatar that may be modified pertain to ethnicity, genetics, gender, weight, artery and vein sizes (which may change dynamically based on a patient's blood pressure, body fat percentage, cholesterol, genetic predispositions, etc.). In short, the generic avatar may be modified in respect of any macro or micro anatomical structure. A separate neural network may be trained for each anatomical structure.

The computer-implemented method of FIG. 3 comprises generating, at step S24, the patient-specific avatar by modifying the generic avatar based on the determined change.

Modifying the patient-specific avatar may comprise retrieving, by the hardware processor, a shape representing the change to the body part and modifying, by the hardware processor, the generic avatar to include the shape representing the change to the body part. For instance, the shape may be spliced with the generic avatar to change the shape of the generic avatar. The shape may comprise a polygon or a polyhedral depending on whether the avatar is presented in two dimensions or three dimensions. The polygons represent the physiological state described by the medical information. For example, if the medical information comprises information that the patient is obese, modifying the generic avatar may comprise modifying the generic avatar to incorporate a polygon at the torso of the generic avatar. For example, the shape corresponding to obesity may comprise a ring shape, and the ring shape may be spliced with the generic avatar shape at the waist section. In this way, the waist may become larger.

Modifying the generic avatar may comprise one or more of translating, scaling, rotating and colouring at least a part of the generic avatar. For example, if the medical information comprises information related to the patient having a skin condition, modifying the generic avatar may comprise changing the colour of the avatar. For example, if the medical information is related to the patient having a swollen body part, modifying the generic avatar may comprise enlarging that body part by scaling up the body part. For example, if the medical information is related to the patient having a dislocated joint, modifying the generic avatar may comprise rotating bones forming the joint and/or translating the location of the bones forming the joint.

The generic avatar may comprise a plurality of nodes 11 defined by spatial coordinates, wherein the body part includes one or more of the plurality of nodes. Relatedly, the method may further comprise retrieving, by the hardware processor, the location of the body part from a look-up table. That is, the method may comprise using the look-up table to determine the location of the body part to be changed based on an association between the body part and one or more of the plurality of nodes 11 as stored in the look-up table.

The hardware processor may be configured to allow a user to change a view of the avatar on a display. For instance, the avatar may be rotatable about one or more of the sagittal plane (lateral), the coronal (frontal) plane and the transverse (axial) plane. For instance, the hardware processor may be configured to allow zooming in or out in response to user input.

Steps of the method of FIG. 1 may be combined with steps of the method of FIG. 2. For example, the method of FIG. 2 may further comprise steps corresponding to those of Figure as required to annotate the patient-specific avatar.

A non-transitory computer-readable medium including instructions stored thereon that, when executed by a hardware processor, cause the hardware processor to perform shown in FIG. 3 is provided.

Figure 4:
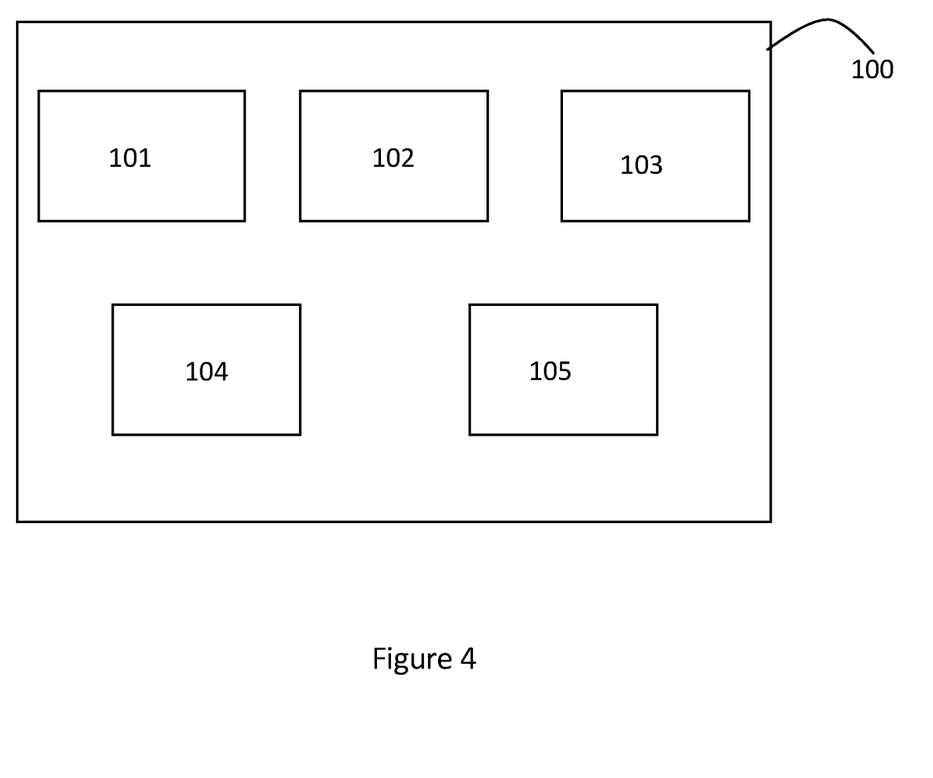
FIG. 4 schematically depicts a system for performing the method shown in FIG. 1 or FIG. 2 according to an exemplary embodiment.

FIG. 4 schematically depicts the hardware processor 100 for performing the method shown in FIG. 1 or FIG. 3 according to an exemplary embodiment. FIG. 4 includes an avatar providing unit 101 configured to provide (e.g., generate) the avatar as in step S11 of FIG. 1 or the generic avatar of step S21 of FIG. 3. The avatar providing unit is further configured to annotate the avatar as described in relation to step S14 of FIG. 1 or modify the generic avatar as described in relation to S24 of FIG. 3. Alternatively, as separate unit may be configured the steps S14 and/or S24. FIG. 4 includes a unit 102 for retrieving the electronic data from the blockchain as described in relation to steps S12 and S22 of FIGS. 1 and 3. FIG. 4 incudes a machine learning unit 103 comprising the machine learning algorithm described in relation to FIG. 1 or FIG. 3. As shown in FIG. 4 and as alluded to earlier, the hardware processor may also comprise a storage unit 104, which may store the avatar of the method of FIG. 1 or the generic avatar of the method of FIG. 3, look-up tables and medical information.

The hardware processor may also comprise a display control unit 105 configured to control display of the annotated or modified avatar.

In summary, there is provided a computer-implemented method of assigning medical information to an avatar representative of a human body that facilitates collation, updating and accessing of an individual's entire care history in real time in a secure and automated manner. The is also provided a computer-implemented method of generating a patient-specific avatar that facilitates personalised medicine is a secure and automated manner.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The disclosure is not restricted to the details of the foregoing embodiment(s). The disclosure extends to any novel one, or any novel combination, of the features disclosed in this specification (including any accompanying claims, abstract and drawings), or to any novel one, or any novel combination, of the steps of any method or process so disclosed.

The invention claimed is:

1. A computer-implemented method of generating a patient-specific avatar performed by a computer including a hardware processor, the method comprising:
    providing, by the hardware processor, a generic avatar representative of a human body;
    retrieving, by the hardware processor, electronic data from a blockchain, the electronic data describing medical information associated with a patient;
    applying, by the hardware processor, the electronic data to one or more machine learning algorithms trained to determine a change to a body part of the generic avatar based on the medical information; and
    generating the patient-specific avatar by modifying the generic avatar based on the determined change,
    wherein the patient-specific avatar is rotatable about the sagittal plane, the coronal plane and the transverse plane.

2. The computer-implemented method of claim 1, wherein the medical information comprises at least one of: text and an image.

3. The computer-implemented method of claim 2, wherein, when the medical information comprises an image, the image at least one of: a radiogram, a tomogram, a thermogram, a magnetic resonance imaging scan image, a positron emission tomography scan image, an ultrasound image, a photoacoustic image, a retinal image and an elastogram image.

4. The computer-implemented method of claim 1, wherein the one or more machine learning algorithms comprises a neural network.

5. The computer-implemented method of claim 1, further comprising:
    applying the retrieved electronic data to an unsupervised clustering algorithm to cluster the retrieved electronic data into groups, where each group is associated with a body part.

6. The computer-implemented method of claim 1, wherein modifying the patient-specific avatar comprises:
    retrieving, by the hardware processor, a shape representing the change to the body part; and
    modifying, by the hardware processor, the generic avatar to include the shape representing the change to the body part.

7. The computer-implemented method of claim 6, wherein the modifying the generic avatar comprises at least one of: translating, scaling, rotating and colouring at least a part of the generic avatar.

8. The computer-implemented method of claim 1, wherein the generic avatar comprises a plurality of nodes defined by spatial coordinates, wherein the body part includes one or more of the plurality of nodes.

9. A computer-implemented method of annotating an avatar representative of a human body with medical information associated with a patient, the method performed by a computer including a hardware processor, the method comprising:
    providing, by the hardware processor, the avatar;
    retrieving, by the hardware processor, electronic data from a blockchain, the electronic data describing the medical information;
    applying the electronic data, by the hardware processor, to one or more machine learning algorithms trained to associate the medical information with a body part from amongst a plurality of body parts of the human body; and
    annotating, by the hardware processor, the avatar with the medical information at a location of the associated body part,
    wherein the avatar is rotatable about the sagittal plane, the coronal plane and the transverse plane.

10. The computer-implemented method of claim 9, wherein the medical information comprises at least one of: text and an image.

11. The computer-implemented method of claim 10, wherein, when the medical information comprises an image, the image comprises at least one of: a radiogram, a tomogram, a thermogram, a magnetic resonance imaging scan image, a positron emission tomography scan image, an ultrasound image, a photoacoustic image, a retinal image and an elastogram image.

12. The computer-implemented method of claim 9, wherein the one or more machine learning algorithms comprises a neural network.

13. The computer-implemented method of claim 10, further comprising:
    when the medical information comprises text, pre-processing, by the hardware processor, the retrieved electronic data to tokenise the text.

14. The computer-implemented method of claim 9, further comprising:
    applying, by the hardware processor, the retrieved electronic data to an unsupervised clustering algorithm to cluster the retrieved electronic data into groups, where each group is associated with a body part.

15. The computer-implemented method of claim 9, wherein annotating the avatar comprises:
    retrieving, by the hardware processor, an anatomical region of the avatar corresponding to the location of the body part; and storing, by the hardware processor, the medical information at the anatomical region on the avatar.

16. The computer-implemented method of claim 15, further comprising:

displaying, by the hardware processor, the annotation when a user input is located over the anatomical region; and concealing, by the hardware processor, the annotation when the user input is not located over the anatomical region.

17. The computer-implemented method of claim 9, wherein the avatar comprises a plurality of nodes defined by spatial coordinates, wherein the associated body part includes one or more of the plurality of nodes, and wherein the location of the associated body part is associated with one of the plurality of nodes.

18. A non-transitory computer-readable medium including instructions stored thereon that, when executed by a hardware processor, cause the hardware processor to perform the method of claim 9.

\* \* \* \* \*